(12) United States Patent
Benedetti

(10) Patent No.: US 9,415,429 B2
(45) Date of Patent: Aug. 16, 2016

(54) PLANT FOR CLEANING BINS USED FOR VEGETABLE PRODUCE

(75) Inventor: Luca Benedetti, Ravenna (IT)

(73) Assignee: UNITEC S.P.A., Lugo, Ravenna (IT)

( * ) Notice: Subject to any disclaimer, the term of this patent is extended or adjusted under 35 U.S.C. 154(b) by 1075 days.

(21) Appl. No.: 13/394,616

(22) PCT Filed: Nov. 9, 2010

(86) PCT No.: PCT/EP2010/067131
§ 371 (c)(1),
(2), (4) Date: Mar. 7, 2012

(87) PCT Pub. No.: WO2011/061097
PCT Pub. Date: May 26, 2011

(65) Prior Publication Data
US 2012/0204918 A1    Aug. 16, 2012

(30) Foreign Application Priority Data
Nov. 19, 2009   (IT) .............................. PN2009A0068

(51) Int. Cl.
*B08B 9/46* (2006.01)
*B08B 3/04* (2006.01)
(Continued)

(52) U.S. Cl.
CPC . *B08B 9/46* (2013.01); *B08B 3/041* (2013.01); *B08B 9/0826* (2013.01);
(Continued)

(58) Field of Classification Search
CPC .... B08B 9/0861; B08B 9/083; B08B 9/0821; B08B 9/20; B08B 9/205; B08B 9/44; B08B 3/041; B08B 9/42; B08B 9/0826; B08B 9/46; A61L 2202/14; G01N 21/90; G01N 21/9018

USPC ......................................... 134/62, 56 R, 57 R
See application file for complete search history.

(56) References Cited

U.S. PATENT DOCUMENTS

| | | |
|---|---|---|
| 4,515,275 A | 5/1985 | Mills et al. |
| 4,534,470 A | 8/1985 | Mills |

(Continued)

FOREIGN PATENT DOCUMENTS

| | | |
|---|---|---|
| DE | 196 26 137 | 1/1998 |
| DE | 198 27 739 | 12/1999 |

(Continued)

*Primary Examiner* — Joseph L Perrin
*Assistant Examiner* — Kevin G Lee
(74) *Attorney, Agent, or Firm* — Davis & Bujold PLLC; Michael J. Bujold

(57) ABSTRACT

A bin cleaning plant includes a bin destacking and overturning station, a plurality of bin washing stations, the whole being connected to a conveyor that transfers the bins in an orderly, continuous and sequential manner through the stations; and means that sense and measure the level of dirt present in each of said bins and that modify the washing process selectively for each of said bins according to the level of dirtiness detected. Preferably, the measurement and control means are connected to optical devices oriented toward the internal surfaces of the bins, and detect the optical/luminous/chromatic image reflected from their internal surfaces. The image is converted into one or more electrical signals with representative characteristics, which signals are compared with corresponding levels selectively predetermined and previously memorized. The measuring and control means control actuators suitable to control/drive one or more of the operating parameters of the washing station.

8 Claims, 4 Drawing Sheets

(51) Int. Cl.
*G01N 21/90* (2006.01)
*B08B 9/42* (2006.01)
*B08B 9/44* (2006.01)
*B08B 3/00* (2006.01)
*B08B 9/08* (2006.01)
*B08B 13/00* (2006.01)

(52) U.S. Cl.
CPC ......... *B08B 9/0861* (2013.01); *G01N 21/9018* (2013.01); *B08B 3/00* (2013.01); *B08B 9/08* (2013.01); *B08B 9/42* (2013.01); *B08B 9/44* (2013.01); *B08B 13/00* (2013.01)

(56) References Cited

U.S. PATENT DOCUMENTS

| | | | |
|---|---|---|---|
| 4,726,898 A | | 2/1988 | Mills et al. |
| 5,398,818 A | * | 3/1995 | McGarvey ............... 209/580 |
| 5,411,042 A | * | 5/1995 | Suzuki ............... A47L 15/0026 |
| | | | 134/105 |
| 5,569,606 A | * | 10/1996 | Fine et al. ............... 436/43 |
| 5,662,226 A | * | 9/1997 | Till ............... 209/2 |
| 5,673,113 A | | 9/1997 | Blanc |
| 5,791,497 A | | 8/1998 | Campbell et al. |
| 5,808,305 A | | 9/1998 | Leidecker et al. |
| 6,524,394 B2 | * | 2/2003 | Okazawa ............... B24C 1/003 |
| | | | 134/18 |
| 6,561,203 B2 | * | 5/2003 | Kajiura et al. ............... 134/127 |
| 6,847,447 B2 | | 1/2005 | Ozanich |
| 7,398,789 B1 | | 7/2008 | Herrera |
| 8,574,371 B2 | * | 11/2013 | Folz ............... B08B 9/38 |
| | | | 134/22.1 |
| 2003/0150475 A1 | | 8/2003 | Abrams et al. |
| 2010/0328476 A1 | * | 12/2010 | Wagner ............... 348/222.1 |

FOREIGN PATENT DOCUMENTS

| | | |
|---|---|---|
| DE | 199 05 933 | 8/2000 |
| DE | 101 51 531 | 7/2002 |
| EP | 0 137 416 | 4/1985 |
| EP | 0 815 962 | 1/1998 |
| EP | 0 847 813 | 6/1998 |
| EP | 0 965 542 | 12/1999 |
| EP | 1 803 507 | 7/2007 |
| EP | 1 967 467 | 9/2008 |
| WO | 85/03622 | 8/1985 |
| WO | 00/13808 | 3/2000 |
| WO | 2006/058406 | 6/2006 |
| WO | 2006/099680 | 9/2006 |
| WO | 2006/117103 | 11/2006 |
| WO | 2009/066020 | 5/2009 |

* cited by examiner

PLANT FOR CLEANING BINS USED FOR VEGETABLE PRODUCE

The present invention relates to an improved plant for the automatic and sequential cleaning of containers, or "bins" as thy will be referred to hereafter, specially used for harvesting vegetable products, in particular fruit.

It is well known that containers of this type are used directly in the fields and, at any rate in close relationship with the soil in order to be filled with the fruit during the relative harvest.

Thus, these containers tend to be carried, handled and filled in a rather rough manner, and often they are also dragged on the ground or set down on it.

In addition, during their use, and particularly when they are being filled and carried, they are inevitably dirtied or contaminated by various agents, such as for example mainly semiliquid material that drips or separates directly from the produce, and that often turns to sugar that can nourish spores, moulds, etc., but also by fragments detached from the collected fruit, or also by other agricultural contaminants, chips of wood, leaf fragments, etc.

As these containers are subsequently used repeatedly on the processing lines for packaging already sorted produce, they must necessarily, even for regulatory reasons, be rigorously cleaned of any residue from the previous batch and processing cycle, it is a customary and required practice to have the same containers undergo a cleaning or washing treatment.

This is carried out, according to the prior art, by providing a continuous conveyor made up of a succession of carrying and conveying means suitable to transfer the containers in an orderly progression through an appropriate washing tank.

Said conveying means are engaged by a sequence of bins, that are thus carried, in a corresponding orderly sequence, to where they are immersed in the washing tank, as shown schematically in FIG. 1.

At the end of said washing operation, the bins are removed from the same tank and then released and made available for the next reutilization.

The bin washing operation is a simple and safe procedure, and of undoubted effectiveness. However, this operation of washing every single bin demands a certain amount of time; thus it is evident that, if there is a large number of bins to wash, as is commonly the case, the total time of engagement and operation of the washing plant becomes correspondingly long.

This involves obvious costs due both to the employment of the personnel handling the bins and to the direct cost of operating the washing plant.

This situation would still be acceptable if all the bins were dirty and thus all of them, without exception, required a complete washing treatment; however, the common experience is that, contrary to what was imagined, only a rather low percentage of bins are actually dirty and needing to be completely washed.

Most of the bins may instead be only partially dirty, or could also not be dirty at all.

On the other hand, the process illustrated is of industrial type, that is, all the bins received and accumulated are brought into the washing plant, regardless of whether any of them are clean or dirty.

The logical consequence of this situation is also that bins that are clean or almost clean are also brought into the plant to be washed, even if this operation would not be absolutely necessary, given that they are still acceptably clean; or it may also be that the bins are only in a partially dirty condition, which would require only a milder and more limited, and therefore less costly washing, both in terms of use of plant and personnel, and in terms of a faster turnaround time for a given number of bins.

And, as a final result, it will be evident that said bin washing plant, and the relative process, generate an inevitable productive inefficiency, with relative extra costs, caused not so much by the state of efficiency of the plant itself, but by the fact that it "processes" indiscriminately all the bins brought into it, regardless of their different conditions of cleanness.

The following patents, DE 199 05 933, EP 1 967 467, WO 2006/117103, EP 0 137 416, WO 2006/099680 A1, EP 0 965 542, U.S. Pat. No. 7,398,789, disclose a lorry for the collection of waste bins, for example household or municipal waste, provided with a relative plant for washing the bins placed in it.

However, in this type of application the washing process can also be avoided, because the type of work to carry out is not of industrial type, but, on the contrary, the operator, generally well advised, can decide each time whether in addition to emptying the bins, it is also necessary to wash them.

However, this possibility is precluded in the automatic bin-washing plants used in agriculture, because the bins are gathered, suitably stacked and placed by non-specialized personnel on a continuous conveyor that carries them into the washing plant; apart from this procedure, said plants are not capable of providing, in a completely automatic manner, a washing treatment that fits the degree of dirt found in each bin.

Moreover, and in this lies the fundamental difference, the bins used to hold agricultural produce must undergo a cleaning procedure that is much more intense and efficient than is the case with the bins generally used to collect waste in the streets and in the collection of household waste; this is due to the easily appreciated reason that the bins for agricultural uses are expected to contain again agricultural produce for human consumption, and therefore they must be scrupulously washed and sanitized, while the bins used for waste collection serve only to collect other waste, and therefore for these bins it is not necessary to provide an extreme cleaning/washing treatment.

Patents EP 1 803 507A2 and EP 0 847 813 B1 disclose the washing of bins used in agriculture, said washing having the same purpose previously described. According to said patents, the bins are tipped over (and thus after the rotation their bottom is at the top), and are sprayed with jets of liquid with various characteristics and manners. However, even in these cases no problem is presented that is in any way similar to the problem described above, nor is a solution disclosed that is capable of effectively solving in an efficient way said problem of a separate washing graduated to fit the degree of dirt found in each individual bin.

Therefore, it would be desirable, and it is the main objective of the present invention, to be able to develop a type of automatic plant for washing/cleaning a continuous sequence of containers/bins for fruit and vegetable produce, suitable to carry out a treatment appropriate for the degree of cleanness of every individual bin, and that is capable of substantially reducing the shortcomings described above.

This objective is achieved by a plant and a relative process achieved and operating according to the attached claims.

Characteristics and advantages of the invention will become evident from the following description, given by way of non-limiting example, with reference to the enclosed drawings, wherein.

Figure 1:
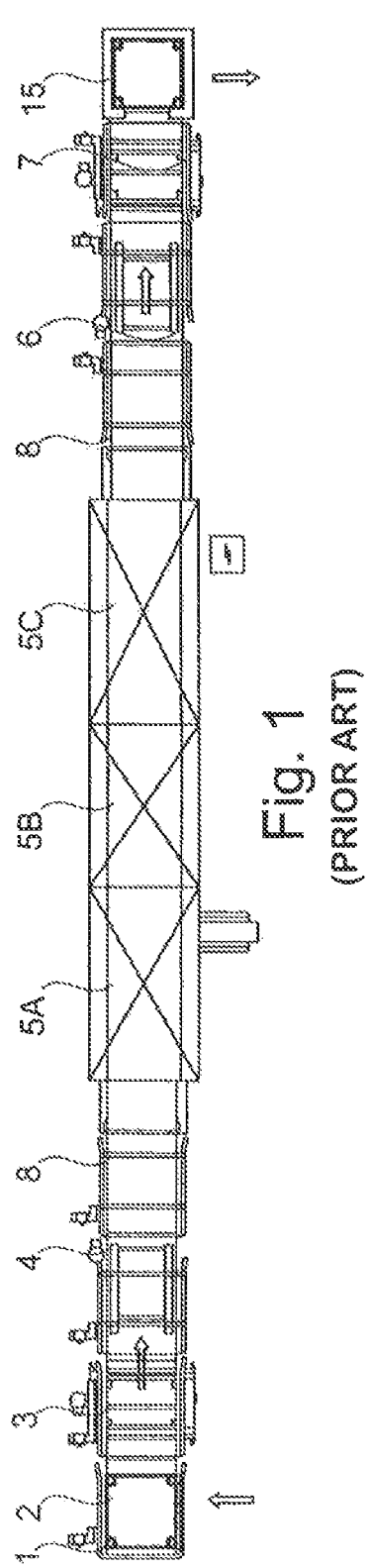
FIG. 1 shows a plane view from above of the schematic embodiment of a plant according to the known art.

With reference to FIG. 1, a plant for the automatic washing of bins used for the collection and transportation of agricultural produce and built according to the known art comprises:

an entry station 1 for dirty and stacked bins 2; a bin destacking station 3;

a bin overturning station 4;

a plurality of bin washing stations 5A, 5B, 5C;

a bin uprighting station 6;

a bin stacking station 7;

a station 15 for the exit of washed and stacked bins 2;

a conveyor 8 that transfers in a continuous, orderly and sequential manner the various bins in transit in the subsequent stations, in a well-known manner.

Said washing stations 5A, 5B and 5C are built to carry out some respective and specific operations of washing the bins that move through them, and they use means, procedures and products that are already known, and for this reason they are not explained further herein.

The plant is integrated, according to the present invention, by means and modes of controlling and measuring the degree of dirtiness present on the internal surfaces of the bins to be washed.

More generally, different techniques may be used to measure the degree of dirt inside the bins; for example, chemical means/sensors may be used, or optical means through the examination of the characteristics of reflected light, etc.

However, by far the preferred and chosen method has turned out to be one of the many methods of optical investigation of the characteristics of said internal surfaces, both in terms of reflected colour and in terms of analysis of the reflected light spectrum, and possibly also of the spectrum reflected outside the visible band, as in the infrared, or also in the U.V. band.

It is appropriate to remember that the technique of the examination of reflected light to characterize the products has been widely known and applied in the art for decades, and particularly for the analysis and selection of vegetable products.

For this reason, and only for the purpose of documenting and supporting the above assertion, the following patents are cited, chosen from tens of patents that disclose different techniques of testing the various characteristics of the spectrum of reflected light:

>>WO 85/03622, —U.S. Pat. No. 4,515,275—U.S. Pat. No. 5,808,305—U.S. Pat. No. 4,534,470—WO 2009/066020—U.S. Pat. No. 5,791,497—U.S. Pat. No. 4,726,898—U.S. Pat. No. 6,847,447 B2—U.S. Pat. No. 5,673,113—WO 2006/058406 A1—WO 00/13808.

Figure 2:
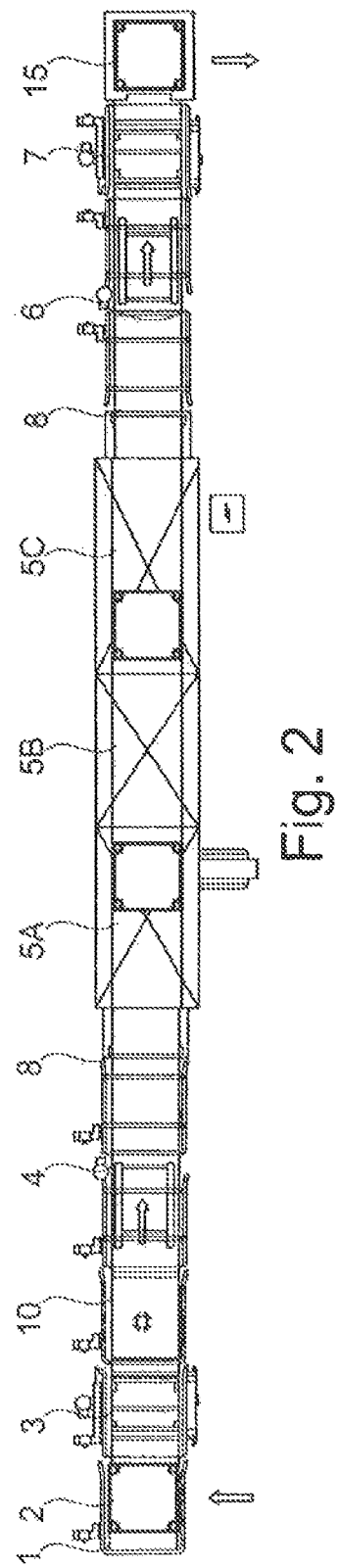
FIG. 2 shows a plane view from above of the schematic embodiment of a modified and improved plant according to the invention.
Figure 3:
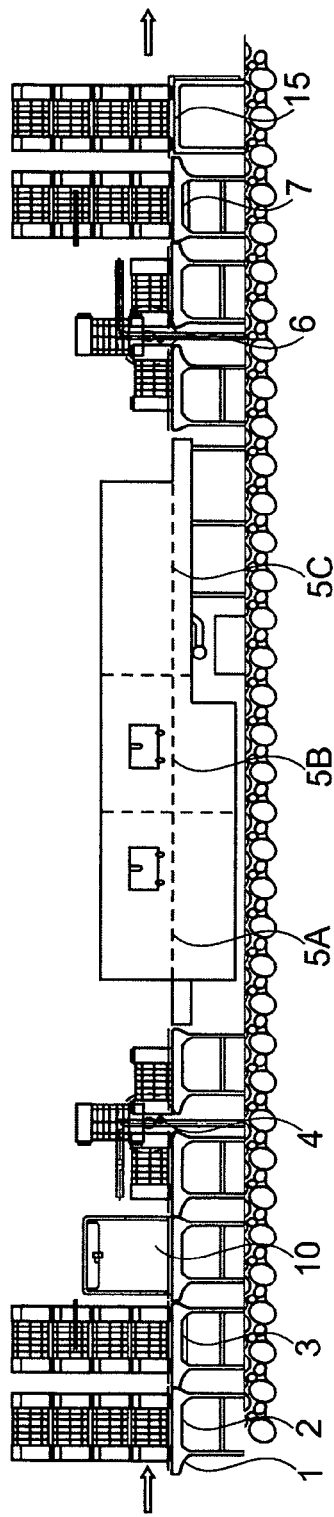
FIG. 3 illustrates a lateral and transversal plane view of the plant of FIG. 2, suitably schematized.

FIG. 2 illustrates schematically a plant according to the invention: in addition to the components/devices already described in FIG. 1, the plant according to the invention is also provided with known optical devices 10, suitable to receive the image or the reflected light from the internal walls of the bins before they are washed.

Figure 6:
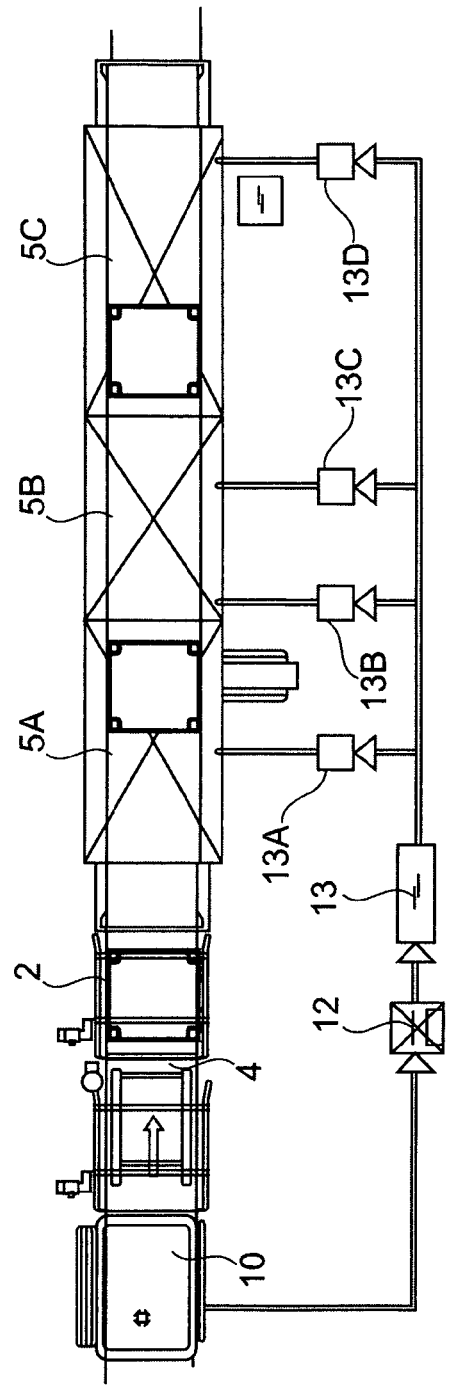
FIG. 6 shows a simplified logical block diagram form of the plant according to the invention.

With reference to FIG. 6, said optical devices 10 convert the light image received into a corresponding electrical signal having the spectral, amplitude and intensity characteristics univically dependent on the characteristics of the reflected and received light.

According to universally known mode of process control, said signal is sent to a measuring and control means 12 wherein specific levels of amplitude or of another characteristic of a reference signal were previously stored.

The signal generated by said optical devices 10 is then compared with one of said levels already stored in said measuring and control means 12, in the sense that the levels of the quantities that can be distinguished in it are compared with the levels of the similar quantities of the reference signal.

Therefore, depending on the result of this comparison, which may also consist of a plurality of comparisons, a further appropriate signal is sent to a relevant memory register that stores such signal and associates it with a definite bin, naturally in the sense that in reality the position of a bin is associated with the bin itself.

At this point, that bin is "indexed" with the data resulting from said comparison in said measuring and control means 12.

These data are then transmitted to a processing and control unit 13 which processes, on the basis of the previously set algorithms and/or functions, the instructions to give to suitable actuators 13A, 13B, 13C, 13D.

These actuators carry out the commands given to them, so that a sequence of washing steps can be carried out consistently with said functions and/or algorithms and therefore aimed at the degree of dirt detected; naturally, the procedure will have to take into account the fact that these actuators must wait to carry out their action only when the bin, for which the degree of dirt has been predetermined, and therefore the relative washing procedure, actually goes through the various washing stages indicated with letters 5A, 5B, 5C, etc.

The parameters that normally must be controlled, and on which said actuators must act, regard in general those parameters that have a main influence on washing intensity and efficiency, and therefore, but not only, the following ones:

the temperature of the liquid for each washing step;

the duration of washing for each step;

the pressure of the washing liquid;

the concentration and the type of substance/detergent used;

the transit speed of the bins through the various washing steps;

etc.

At the end of the washing steps, the bins proceed on their course programmed according to the known art through the bin uprighting station 6 and the stacking station 7.

It will therefore be evident that at this point all the bins have been treated, that is, washed, exactly in function of their degree of dirtiness and according to the intensity of the pre-programmed washing action that corresponds to the relative degree of dirtiness.

Figure 4:
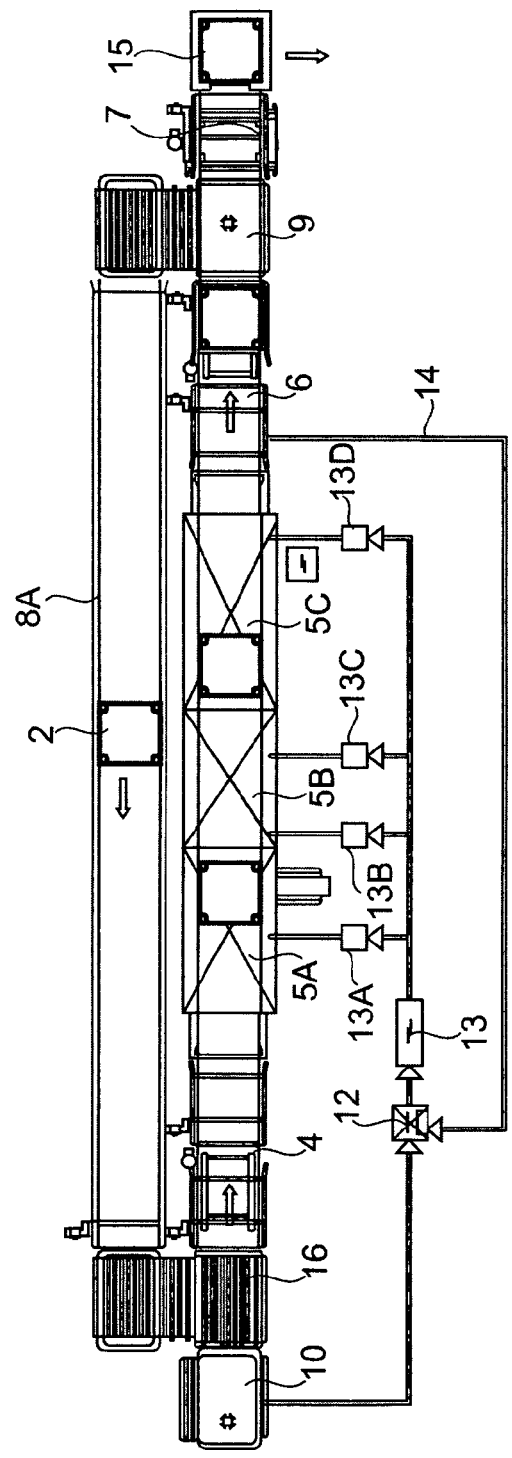
FIG. 4 shows a view similar to FIG. 2 but relative to an improved embodiment and manner of operation of a plant according to the invention.
Figure 5:
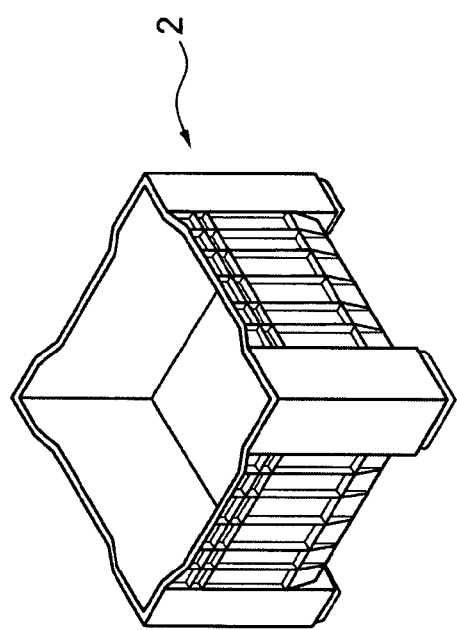
FIG. 5 shows a perspective view of a typical container or bin used by the plant according to the invention.
Figure 7:
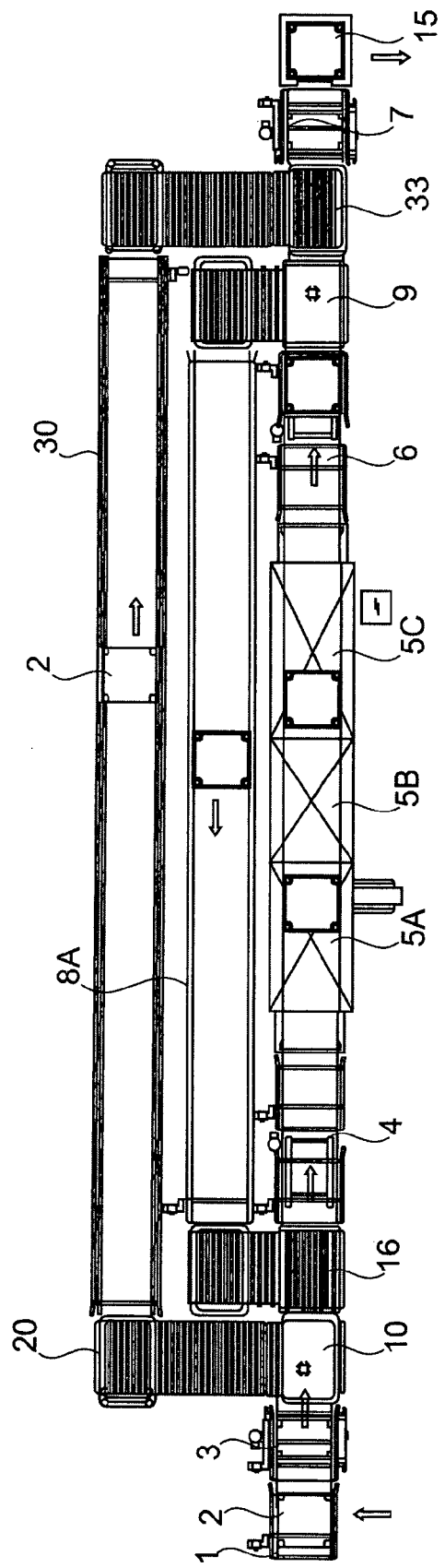
FIG. 7 illustrates another diagram similar to FIG. 2 but showing still another different and advantageous improved embodiment of the invention.

The invention as described to this point is also susceptible to advantageous improvements, A) With reference to FIGS. 4 and 7, after the washing stations 5A, 5B, 50 and the bin uprighting station 6, there is a checking and measuring station 9 completely similar to the station in which the optical device 10 has been arranged to measure the degree of dirtiness of the bin and is preferably connected to said measuring and control means 12 through a suitable connection 14; the purpose of said further checking station 9 equipped with an optical device similar to the device 10 consists in the elimination of the possibility that any bin, although measured and correctly washed according to its degree of dirtiness consistently with the pre-programmed procedures, still remains too dirty, or unacceptably dirty, said condition being due to various causes, such as for example a particular resistance or nature of the dirt, or also due to a faulty programming of the processing and control means 13.

Therefore, the presence of the station 9 added after the washing stages ensures that the degree of residual dirt in each bin is measured again to check the effectiveness of the washing action, and if this degree is not considered acceptable, according to the previous procedures and means, the bins that are found to be still "dirty" are shunted out of the conveyor 8, and thus removed from the normal flow of bins moving toward the stacker 7, and sent back, through a return conveyor 8A, to a suitable station 16, to be reprocessed/washed. It is also evident that said additional station 9 transmits again the signals produced to said measuring and control means 12 already defined, or to means that are completely similar but that are however capable of carrying out the described "filtering" action, that is to allow the bins going through said further checking and measuring station 9 to pass or to be shunted. Advantageously, said additional checking station 9 is arranged downstream of the uprighting station 6 for the purpose of replicating most effectively the existing conditions of operation of said optical devices 10.

B) A further improvement is illustrated in FIG. 7, which shows an embodiment of a similar plant which however makes it possible, in the likely case that some bin is already sufficiently clean before entering the washing stations, to skip washing said bin. Naturally, this possibility is precious, as it makes it possible to avoid having to bear unnecessary burdens in terms of plant use and labour, as well as in terms of demands for power, water, washing substances, etc.

For this purpose, when said circumstance occurs, and it is naturally measured and established by said measuring and control means 12, according to the known procedures, said measuring means 12 generate a suitable instruction (not shown) that is sent to a supplementary shunting station 20 located immediately downstream of said optical devices 10.

Said station 20 is enabled to shunt those bins that turn out to be sufficiently clean away from the conveyor 8 and onto a parallel conveyor 30 that bypasses said washing stations 5A, 5B, 5C and that reintroduces the relative bins directly into a suitable re-entry station 33 located downstream of the washing stations and of the uprighting station 6, and thus upstream of the stacking station 7.

C) The third improvement consists in the fact of arranging lighting means, of known types and not shown, in a suitable position by said optical devices 10, and in the further checking station 9; the purpose of said lighting means is to light up in a constant and known manner the surfaces of the bins having a reflected light and hue to be measured, so as to eliminate any variables due to ambient light, such as flashes of light, changes in the sun's brightness, etc., and so as to ensure that the light reflected from the bin surfaces is substantially dependent only from their nature and colouring, and to be able to effectively carry out much more accurate and reliable measurements.

D) The fourth improvement results from the possibility that the dominant colour of the bin (which of course is coloured uniformly with a definite colour) is confused by said measuring and control means 12 with a particularly substantial degree of dirt and with an intensity such as to be classified as "very dirty", and therefore to require a particularly intense washing cycle. If this requirement is not actually the case, the application of such an energetic washing cycle translates into an unnecessary economic burden, without any real benefit. To eliminate such drawback, both said optical devices 10 and checking station 9 and the measuring and control means 12 are equipped with devices for discriminating the optical image and processing the relative electrical signal so as to identify a likely dominant colour, as defined in the technical language, and to process the optical image transmitted by the bin and received, having as reference for said processing said colour defined as dominant. In practice, said identified colour defined as dominant is compared with (or subtracted from) the optical image received, and the result of said processing is then used to classify the nature and intensity of the dirt and thus to select the corresponding washing cycle. The necessary optical and electronic processing means, and the relative processes and modes of operation are known and easily available to a person of average skill in the art, and for this reason they are not explained further herein.

The invention claimed is:

1. An automated cleaning bin system for cleaning a continuous sequence of bins suitable for carrying vegetables and fruit produce, the system to carry out a tailored treatment appropriate for each individual bin of the continuous sequence of bins according to a degree of cleanliness for each individual bin, said automated system comprising:
   an automated entry station configured for accepting into the system the continuous sequence of bins in a stacked configuration;
   an automated bin de-stacking station, configured for unstacking the stacked configuration of the continuous sequence of bins, the continuous sequence of bins;
   an automated bin overturning station, configured for inverting each bin;
   an automated restoring station, configured for again overturning the bins inverted by said overturning station;
   an automated bin re-stacking station, configured for re-stacking the continuous sequence of bins in a second stacked configuration; and
   a control device configured for storing specific reference characteristics, receiving signals relating to the degree of dirtiness of each individual bin, receiving signals of the position of each individual bin, indexing each individual bin, comparing the received signals with the stored specific reference characteristics, and sending instructions relating to the degree of dirtiness detected, to a remainder of the automated system, thus the control device is connected to the remainder of the automated system which further comprises:
   a plurality of automated sensor stations being configured for measuring the position and degree of dirtiness present on an internal surface of each individual bin, and configured for sending the signals of the degree of dirtiness and position to the control device;
   the plurality of sensor stations including a first sensor station being an optical sensor station, and a second sensor station being one of either an ultraviolet sensor and an infrared sensor;
   an automated plurality plurality of separate, independently operating bin washing stations arranged in series including at least a first bin washing station a second bin washing station, and a third bin washing station;
   a first operating actuator, of the first bin washing station, being configured for receiving signals of the degree of dirtiness and the position of the bin and initiating an operating condition of the first bin washing station for a working time-length having a duration of washing beginning when the bin enters and ending when the bin exits the first bin washing station thus operating independently with respect to a rest of the plurality of washing stations;

a second operating actuator, of the second bin washing station, configured for receiving signals of ha degree of dirtiness and the position of the bin and initiating an operating condition of the second bin washing station for a working time-length beginning when the bin enters and ending when the bin exits the second bin washing station thus, operating independently with respect to the rest of the plurality of washing stations; and a third operating actuator, of the third bin washing station, configured for receiving signals of the degree of dirtiness and the position of the bin and initiating an operating condition of the third bin washing station for a working time-length beginning when the bin enters and ending when the bin exits the third bin washing station, thus operating independently with respect to the rest of the plurality of washing stations;

each of the operating actuators of the plurality of bin washing stations independently sets the working time-length of each respective plurality of bin washing stations based on the degree of dirtiness according to the signals;

an automated conveyor system configured for transferring each of the continuous sequence of bins to each station of the system, in a continuous, orderly and sequential manner, according to the received instructions relating to the degree of dirtiness detected, respectively;

the first automated sensor station, upstream of the first bin washing station, being configured for measuring the degree of dirtiness present on the internal surface of each individual bin initially, and configured for sending the signals of the degree of dirtiness and position to the control device;

a first automated shunting station, downstream of the first automated sensor station and upstream of the first bin washing station being configured for diverting bins according to the instructions relating to the degree of dirtiness detected, such that: when the degree of dirtiness is above a level of pre-definable data, the bin is conveyed upstream towards the first bin washing station, and when the respective dirt degree is below the level of pre-definable data, the bin is diverted downstream beyond the third bin washing station;

the second automated sensor station, downstream of at least the third bin washing station, being configured for measuring the degree of dirtiness present on the internal surface of each individual bin residually, and configured for sending the signals of the degree of dirtiness and position to the control device; and a second automated shunting station, downstream of the second automated sensor station, being configured for diverting bins according to instructions relating to the degree of dirtiness detected, such that: when the degree of dirtiness is above the level of pre-definable data, the bin is diverted back upstream towards the first bin washing station, and when the respective dirt degree is below the level of pre-definable data, the bin is conveyed downstream.

2. The cleaning bin system according to claim 1, wherein each operating actuator of the plurality of bin washing stations further includes the following:
   a washing temperature actuator,
   a washing jet pressure actuator,
   a washing substances choice actuator, and
   a washing substances concentration actuator, and each operating actuator of the plurality of bin washing stations are further configured to independently control one or more working parameters in response to the signals, said working parameters further includes at least one of the following:
   a washing liquor temperature,
   a washing jet pressure,
   a concentration of the washing substances, and
   a kind of said substances, and
   said working parameters each operating actuator of the plurality of bin washing stations includes actuating elements of said conveyor system and said working parameters includes at least controlling and adjusting a moving speed of said bins through said washing stations.

3. The cleaning bin system according to claim 1, wherein said control device comprises at least one data storage device configured for storing pre-definable data corresponding to a pre-defined dirt degree of said bins.

4. The cleaning bin system according to claim 1, further comprising:
   a data storage device configured for storing pre-definable data corresponding to a pre-defined dirt degree of said bins, and
   a second conveyor configured to convey the bins diverted by the first automated shunting station downstream beyond the third bin washing station.

5. The cleaning bin system according to claim 4, further comprising a lining and re-entry station, arranged downstream of said bin washing stations, and said second conveyor conveys the bins up to and into said lining and re-entry station.

6. The cleaning bin system according to claim 1, further comprising a return-conveyor configured to convey the bins diverted by the second automated shunting station upstream towards the first bin washing station, whose residual dirt degree is still not acceptable.

7. The cleaning bin system according to claim 1, further comprising illuminating devices placed in correspondence with the plurality of automated sensor stations.

8. The cleaning bin system according to claim 1, wherein the plurality of automated sensor stations and said control device being configured for detecting the existence of a prevailing color and of discriminating the amplitude and the color of a received optical image with respect to said prevailing color.

* * * * *